United States Patent [19]

Grakauskas

[11] 4,233,249
[45] Nov. 11, 1980

[54] METHOD FOR THE PREPARATION OF ALKALI METAL SALTS OF DINITROMETHANE

[75] Inventor: Vytautos Grakauskas, Arcadia, Calif.

[73] Assignee: The United States of America as represented by the Secretary of the Air Force, Washington, D.C.

[21] Appl. No.: 33,608

[22] Filed: Apr. 26, 1979

[51] Int. Cl.³ ............................................. C07C 76/02
[52] U.S. Cl. .................................................... 568/926
[58] Field of Search ......................... 260/644; 560/156

[56] References Cited

U.S. PATENT DOCUMENTS

| 2,161,475 | 6/1939 | Landon | 260/644 |
| 2,597,027 | 5/1952 | Passino et al. | 260/644 |
| 3,067,261 | 12/1962 | Clark et al. | 260/644 |
| 3,378,596 | 4/1968 | Toops, Jr. et al. | 260/644 |
| 3,387,044 | 6/1968 | Grakauskas et al. | 260/644 |
| 3,706,808 | 12/1972 | Bachman et al. | 260/644 |

*Primary Examiner*—Leland A. Sebastian
*Attorney, Agent, or Firm*—Joseph E. Rusz; William J. O'Brien

[57] ABSTRACT

A method for synthesizing the alkali metal salts of dinitromethane by effecting the direct nitration of methyl malonate followed by the step of saponifying the nitrated reaction product.

5 Claims, No Drawings

METHOD FOR THE PREPARATION OF ALKALI METAL SALTS OF DINITROMETHANE

STATEMENT OF GOVERNMENT INTEREST

The invention described herein may be manufactured and used by or for the Government for governmental purposes without the payment of any royalty thereon.

BACKGROUND OF THE INVENTION

This invention relates to dinitromethane and to a method for preparing its alkali metal salts. In a more particular aspect, this invention concerns itself with a simplified and economical process that permits the convenient synthesis of alkali metal salts of dinitromethane through the use of methyl malonate and methyl dinitroacetate as reaction components.

Dinitromethane and its salts find wide application as starting materials and key intermediates in the synthesis of gemminal dinitro compounds, polynitro explosives and propellants. The wide utilization of these materials serves to illustrate their importance in chemical synthesis. Unfortunately, the lack of a simple and economical procedure for preparing these key intermediates has limited their use and effectiveness and requires the use of expensive and problematic synthesis for their preparation such as those described hereinafter.

It is known from P. Duden, Ber., 26, 3003 (1893) that free dinitromethane is an unstable pale-yellow oil and decomposes vigorously even at ambient temperatures. The alkali metal salts of dinitromethane, however, are quite stable. The potassium salt was first prepared by the reduction of potassium bromonitromethane with hydrogen sulfide in accordance with the method of R. Villiers, Bull. Soc. Chem. Fr., 41, 281 (1884). More recently, potassium dinitromethane has been prepared by the Ter Meer reaction of chloronitromethane as shown in H. Fener et al, J. Arm. Chem. Soc., 73 1360 (1951). Unfortunately, this reaction only produces yields of about 23 percent. The dinitromethane salts can also be obtained from the alkali salts of dinitroethanal according to the methods shown by P. Noble et al, Chem. Rev., 64 19 (1964).

The alkali salts of dinitromethane have proven to be very useful as starting materials in the synethesis of a gemminal dinitro compounds. For example, potassium dinitromethanal reacts readily with one or two moles of formaldehyde to give potassium dinitronethanol and 2,2-dinitropropanediol, respectively. The fluorination of alkali salts of dinitronethanol, in turn, produce fluorodinitroethanol. Fluorodinitromethane and 4,4-dinitropimelic acid are other gemminal dinito intermediates found to be useful in the synthesis of polynitro explosives and propellants.

From the above examples, it can be seen that dinitromethane salts are important reactant materials which find wide application as key intermediates in a variety of chemical syntheses. Consequently, a considerable research effort has evolved in an attempt to find efficient, economical and practical routes for preparing the alkali salts of dinitromethane. Heretofore, the lack of practical routes necessitated the use of methods based on the Ter Meer method, the use of nitrogen or the oxidative nitration reaction.

Nitroform, used in the synthesis of fluorodinitroethanol, is produced by nitration of acetylene or acetone. Both processes produce large amounts of nitrogen oxides which present expensive pollution problems. In its applications, for the synthesis of gemminal dinitro compounds, one nitro group of nitroform must be removed adding to the cost of this process.

In the oxidative nitration route, gem-dinitro compounds are prepared by reacting mononitro compounds with a mixture of silver nitrate and sodium nitrite. In a large scale production, this method requires a large capital investment in silver nitrate and also suffers from mechanical losses of silver.

The Ter Meer reaction is limited to the synthesis of terminal gem-diniro compounds. As already indicated, the yield of dinitromethane in the Ter Meer method is low. Also, in many cases, nitrohalo starting materials needed in this reaction cannot be obtained in good yields. With the present invention, however, the problems associated with the prior art methods have been overcome by a method of synthesis in which the alkali metal salts of dinitromethane are prepared by nitrating methyl malonate to form methyl dinitroacetate. The dinitroacetate is then reacted with sodium or potassium hydroxide to effect its saponification and resulting production of the corresponding alkali metal salt of dinitromethane. This unique method provides a solution to the problem of finding a practical and economical route for synthesizing these useful intermediate reactants in high yield.

SUMMARY OF THE INVENTION

In accordance with this invention, a practical and economical route has been found for synthesizing the alkali metal salts of dinitromethane in relatively high yield. The synthesis is accomplished by effecting the nitration of methyl malonate followed by the step of saponifying the nitrated reaction product to produce the desired alkali metal salt. The best yield of methyl dinitroacete resulting rom the nitration reaction is achieved by using an excess of red fuming nitric acid to effect nitration. However, nitric acid, nitric-sulfuric acid and nitrogen tetaoxide can also be employed as the nitrating agent.

Accordingly, the primary object of this invention is to provide a practical route for the synthesis of the alkali metal salts of dinitromethane.

Another object of this invention is to provide a method for synthesizing the alkali salts of dinitromethane in relatively high yield that is economical and readily adaptable to large scale industrial use.

Still another object of this invention is to provide a method for synthesizing the alkali metal salts of dinitromethane that involves the nitration of methyl malonate followed by the saponification of the resulting nitrated reaction product.

The above and still other objects and advantages of this invention will become more readily apparent upon consideration of the following detailed description thereof.

DETAILED DESCRIPTION OF THE PREFERRED EMBODIMENT

Pursuant to the above-identified objects, the present invention concerns itself with a novel process for synthesizing the alkali metal salts of dinitromethane. The synthesis is accomplished by a reaction which involves the steps of nitrating methyl malonate to produce methyl dinitroacetate in accordance with the following reaction:

$$HO_2CCH_2CO_2CH_3 + HNO_3 \rightarrow HC(NO_2)_2CO_2CH_3 \quad (1)$$

followed by the step of reacting the resulting methyl dinitroacetate reaction product with sodium hydroxide according to the reaction:

$$HC(NO_2)_2CO_2CH_3 + NaOH \rightarrow Na^+CH(NO_2)_2 \quad (2)$$

to effect the sponification of the dinitroacetate and the production of the sodium salt of dinitromethane.

The nitration of malonates is well known and a number of alkyl dinitroacetates have been prepared by Kissenger et al, J. Org. Chem. 23, 1340 (1955) through the nitration of mono-alkyl malonates. However, the Kissenger et al methods only produced yields in the amount of about 10 to 20 percent.

With this invention, however, it has been found that the best yields of methyl dinitroacetate in amounts of from 55 to 60 percent could be achieved by using 20% red fuming nitric acid (ca 4–5 times the weight of the substrate) in methylene chloride at ambient temperatures. A side reaction product of these nitrations, 3,4-bis(carbomethoxy)furazan-2-oxide, could be readily separated from the product. On storage at ambient temperature for several days, methyl dinitroacetate gradually decomposes to the furazan derivative in accordance with the following reaction:

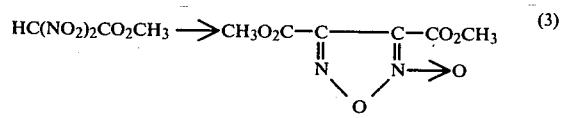

The alkali sales of methyl dinitroacetate, however, are stable and storable for long periods of time (6–8 months).

It was also found that the methyl dinitroacetate underwent rapid saponification at 70° to 80° C. when treated with aqueous alkalies to give the corresponding alkali salts of dinitromethane in yield of 90 to 95 percent according to the reaction:

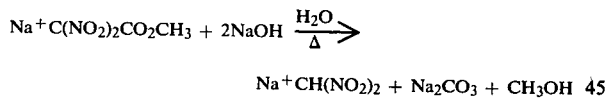

Like the many other alkali salts of gem-dinitro compounds, potassium dinitromethane is sparingly soluble in water whereas the sodium salt is very soluble. Both salts can be stored without any noticeable decomposition for at least several weeks at ambient temperatures. These salts are sensitive to impact and in the larger scale work aqueous solutions of the sodium salt were used for safe handling. Because of their impact sensitivity, these salts should be handled with caution.

The process of this invention may best be understood by referring to the following examples which illustrate specific embodiments of the invention. The examples, however, are presented by way of illustration and are not to be considered as limiting the invention in any way.

EXAMPLE 1

To a stirred solution of 132 g (1.0 mol) of dimethyl malonate in 250 ml of methanol at room temperature was added dropwise (15 min) with occasional cooling a solution of 66 g (1.0 mol) of 85% potassium hydroxide in 150 ml of methanol. After 15 min, the mixture was acidified with 1 mol of concentrated hydrochloric acid and filtered. The filter cake (KC) was washed with two 25-ml portions of methanol. The combined filtrate and washing were concentrated on a rotating evaporator, and the residual liquid was dissolved in 150 ml of methylene chloride. The solution was filtered from a small amount of salts. The filtrate was distilled to give 95 g (80% yield) of methyl malonate: bp 90° C. (0.5 mm); NMR (CDCl$_3$) 3.44 (s,2H), 3.75 (s,3H), and 11.1 (s,COCH).

Methyl malonate was also obtained in 85% yield when diethyl malonate instead of dimethyl malonate was used. Ethyl malonate was obtained in 85% yield from diethyl malonate following the above procedure but using ethanol as the solvent.

EXAMPLE 2

To a stirred and cooled solution of 80 g of 20% red fuming nitric acid in 60 ml of methylene chloride at −5° C. was added 25 g of methyl malonate. After 3 h at 5°–7° C., the reaction mixture was drowned in 150 ml of ice-water. The methylene chloride solution was washed with three 75-ml portions of ice-water drived and concentrated on any rotary evaporator to leave 21 g of crude methyl dinitroacetate (60% yield). An analytical sample was obtained by distillation: bp 37°–38° C. (0.02 mm) [reported[17] bp 38° C. (0.02 mm)] NMB (CDCl$_3$) 4.00 (s,6 H) and 6.75 (s, 1 H).

EXAMPLE 3

To 8.1 g (0.04 mol) of potassium salt of methyl dinitroacetate was added a solution of 2.65 g (0.04 mol) of 85% potassium hydroxide in 30 ml of water and the mixture was heated at 80°–85° for five minutes. The solution was cooled to 0°–5° and potassium dinitroacetate was collected and washed with two 5 ml portions of ice water. The air-dried material weighed 4.9 g (85% yield).

EXAMPLE 4

To a stirred solution of 1.5 g of potassium hydroxide in 15 ml of water was added 4.05 (0.02 mol) of methyl potassium dinitroacetate and the mixture was heated at 65°–70° C. for a few minutes. The deep orange red solution turned turbed and began to deposit some yellow solid. The mixture was cooled to 0°–5° C. The yellow crystalline solid was collected and washed with two 5-ml portions of ice-water. Air-dried solid amounted to 2.6 g (90% yield) mp 220° C.(expl) (reported[4] mp 216° C. dec).

Examples 1 and 2 illustrate, respectively, methods for preparing methyl malonate and methyl dinitroacetate while Examples 3 and 4 both illustrate the preparation of the potassium salt of dinitromethane. Obviously, the sodium salt would be prepared in the same manner by utilizing sodium hydroxide as a reactant material.

From a consideration of the above, it can be seen that the present invention provides a practical and economical route to the synthesis of the alkali metal salts of dinitromethane. Obviously, modifications and variations of the invention are possible in light of the above teachings. It is to be understood, however, that all such modifications as come within the scope of the appended claims are intended to be included herein.

What is claimed is:

1. A method for synthesizing the alkali metal salts of dinitromethane which comprises the steps of (A) effecting a reaction between methyl malonate and a nitrating agent to produce methyl dinitroacetate; and
(B) reacting the resulting methyl dinitroacetate reaction product with an aqueous solution of an alkali metal hydroxide at a temperature of from about 65° C. to 85° C. for a period of time sufficient to produce an alkali salt of dinitromethane.

2. A method in accordance with claim 1, wherein said nitrating agent is selected from the group consisting of red fuming nitric acid, nitric sulfuric acid, nitric acid and nitrogent tetroxide.

3. A method in accordance with claim 1 wherein said nitrating agent is 20 percent red fuming nitric acid.

4. A method in accordance with claim 1 wherein said alkali metal hydroxide is selected from the group consisting of potassium hydroxide and sodium hydroxide.

5. A method in accordance with claim 4 wherein said period of time ranges from about two to five minutes.

* * * * *